United States Patent
Pfanzelt et al.

(10) Patent No.: US 10,744,487 B2
(45) Date of Patent: Aug. 18, 2020

(54) TABLET-FORM COPPER MANGANESE-BASED CATALYST WITH INCREASED STABILITY AGAINST THE ACTION OF ACID

(71) Applicant: CLARIANT INTERNATIONAL LTD, Muttenz (CH)

(72) Inventors: Manuel Pfanzelt, Sauerlach (DE); Martin Paulus, Rosenheim (DE); Frank Grossmann, Munich (DE)

(73) Assignee: CLARIANT INTERNATIONAL LTD, Muttenz (CH)

(*) Notice: Subject to any disclaimer, the term of this patent is extended or adjusted under 35 U.S.C. 154(b) by 0 days.

(21) Appl. No.: 16/464,839

(22) PCT Filed: Nov. 17, 2017

(86) PCT No.: PCT/EP2017/079612
§ 371 (c)(1),
(2) Date: May 29, 2019

(87) PCT Pub. No.: WO2018/108451
PCT Pub. Date: Jun. 21, 2018

(65) Prior Publication Data
US 2019/0321808 A1    Oct. 24, 2019

(30) Foreign Application Priority Data
Dec. 15, 2016 (DE) .......... 10 2016 225 172

(51) Int. Cl.
| | | |
|---|---|---|
| *B01J 23/00* | (2006.01) | |
| *B01J 23/889* | (2006.01) | |
| *B01J 35/02* | (2006.01) | |
| *B01J 35/10* | (2006.01) | |
| *B01J 37/00* | (2006.01) | |
| *B01J 37/10* | (2006.01) | |
| *B01J 37/18* | (2006.01) | |

(52) U.S. Cl.
CPC ......... *B01J 23/002* (2013.01); *B01J 23/8892* (2013.01); *B01J 35/023* (2013.01); *B01J 35/1014* (2013.01); *B01J 37/0018* (2013.01); *B01J 37/10* (2013.01); *B01J 37/18* (2013.01); *B01J 2523/17* (2013.01); *B01J 2523/27* (2013.01); *B01J 2523/31* (2013.01); *B01J 2523/72* (2013.01)

(58) Field of Classification Search
CPC .. B01J 23/8892; B01J 23/002; B01J 2523/00; B01J 2523/17; B01J 2523/27; B01J 2523/31; B01J 2523/72; B01J 35/023; B01J 37/0018; B01J 37/10; B01J 37/18
See application file for complete search history.

(56) References Cited

U.S. PATENT DOCUMENTS

| | | | |
|---|---|---|---|
| 4,126,581 A | 11/1978 | Sugier | |
| 4,871,710 A | 10/1989 | Denny | |
| 5,041,408 A | 8/1991 | King | |
| 5,302,569 A * | 4/1994 | Horn | ............ B01J 23/80 502/238 |
| 6,020,285 A | 2/2000 | Hancock | |
| 6,037,504 A | 3/2000 | Darsow | |
| 7,084,312 B1 | 8/2006 | Huber | |
| 7,465,839 B2 | 12/2008 | Ladebeck | |
| 7,663,003 B2 | 2/2010 | Huber-Dirr | |
| 7,884,046 B2 | 2/2011 | Huber-Dirr | |
| 8,759,594 B2 | 6/2014 | Abillard | |
| 9,579,631 B2 | 2/2017 | Wölk | |
| 10,232,353 B2 | 3/2019 | Lygin | |
| 10,350,577 B2 | 7/2019 | Thakur | |
| 2008/0207953 A1 | 8/2008 | Houssin | |

FOREIGN PATENT DOCUMENTS

| | | | |
|---|---|---|---|
| WO | 9204119 | 3/1992 | |
| WO | 2007006719 | 1/2007 | |
| WO | WO-2016154514 A1 * | 9/2016 | ........... C07C 29/149 |

OTHER PUBLICATIONS

V.I Yakerson "Design of Heterogeneous Catalyic Systems . . . " React. Kinet. Catal. Lett. 55(2), 1995, 455-462.
V.I Yakerson "Scientific bases for the preparation of new cement containing catalysts" Preparation of Catalysts VI, Scientific Bases for the Preparation of Heterogeneous Catalysts 1995, 879, Textbook.
Valentin Antonovic "The Effect of Temperature on the Formation of the Hydrated . . . " Procedia Engineering 57 (2013), 99-106.

* cited by examiner

*Primary Examiner* — Yate' K Cutliff

(57) ABSTRACT

The invention relates to a copper manganese-based catalyst on the basis of a tablet-form shaped catalyst body, comprising calcium aluminate as a binder, for hydrating carbonyl groups in organic compounds, characterised in that said shaped catalyst body comprises calcium aluminate in an amount of 0.5 to 20 wt. %. The invention also relates to the production of the catalyst and to the use of same in the hydration of carbonyl groups in organic compound.

18 Claims, No Drawings

TABLET-FORM COPPER MANGANESE-BASED CATALYST WITH INCREASED STABILITY AGAINST THE ACTION OF ACID

The present invention relates to an improved catalyst based on a tableted shaped catalyst body comprising a material of the formula $CuAl_aMn_bZn_cO_d$ with calcium aluminate as binder material for hydrogenation of carbonyl groups in organic compounds, wherein the shaped catalyst body comprises a proportion of calcium aluminate in an amount of 0.5% to 20% by weight. The present invention additionally also relates to the preparation of the catalyst and to the use thereof in the hydrogenation of carbonyl groups in organic compounds.

BACKGROUND OF THE INVENTION

Catalytic processes for hydrogenation of carbonyl groups in organic compounds such as esters, diesters, aldehydes or ketones are of great relevance in industry. They serve, inter alia, to convert carboxylic acids or their esters, specifically esters of fatty acids, to the corresponding alcohols.

Suitable catalysts here are systems based on copper in combination with further transition metal elements. The catalysts are typically in the form of tablets, extrudates or pellets.

WO 2004/085356 describes the preparation of a catalyst for the hydrogenation of carbonyl compounds which comprises, as well as copper and aluminum, at least one oxide of lanthanum, tungsten, molybdenum, titanium or zirconium, and to which have additionally been added copper powder or flakes, cement powder or graphite.

U.S. Pat. No. 6,020,285 describes the preparation of a cobalt- or nickel-containing catalyst also comprising calcium aluminate with an Al/Ca ratio of greater than 2.5. The catalyst is suitable for breakdown of hypochlorite.

WO 98/11985 discloses cobalt- or nickel-containing catalysts additionally comprising calcium aluminate with an Al/Ca ratio of greater than 4.0, and also alumina and/or magnesia. The catalyst is suitable for breakdown of oxidizing substances.

U.S. Pat. No. 7,084,312 describes the preparation of catalysts based on copper, zinc and aluminum, for which an oxidic mixture of copper, zinc and aluminum is blended with metallic copper, a cement or a mixture of the two materials and shaped to tablets. The catalyst is used for the hydrogenation of organic compounds having carbonyl groups.

Yakerson et al. (Scientific Bases for the Preparation of Heterogeneous Catalysts, Preparation of Catalysts, p. 879 ff.) describes the preparation of cement-containing metal catalysts, for example nickel, copper or zinc catalysts. The corresponding metal hydroxo carbonates are used for this purpose.

The starting compounds in the hydrogenation processes generally include traces of acidic compounds. These are, for example, carboxylic acids present as by-products in esterification reactions. These compounds attack the catalyst under the conditions of the hydrogenation reaction and lead to lowering of mechanical stability and the occasional observation of leaching-out of the catalytically active metals, which are discharged from the reaction reactor with the product stream and have to be separated therefrom. Moreover, there is also a reduction in the catalytic activity of the catalyst with advancing discharge of the catalytically active metals.

Catalysts containing copper and chromium are used for such reactions. These typically have elevated stability to the action of acid. Owing to stricter environmental regulations, the use of chromium catalysts is associated with ever higher demands, and so there is a need to replace the existing CuCr systems with environmentally compatible alternatives that nevertheless have comparable catalytic and physical properties.

It was therefore an object of the present invention to provide a catalyst for hydrogenations of carbonyl groups in organic compounds that features improved mechanical stability and is less prone to the action of acidic compounds.

This object is achieved by the catalyst of the invention.

DESCRIPTION OF THE INVENTION

The invention relates to a shaped catalyst body in tablet form, comprising a material of the formula $CuAl_aMn_bZn_cO_d$ and calcium aluminate as binder material.

a is between 0 and 2.5, b is between 0.001 and 0.6, c is between 0 and 2.5, and d is chosen such that the overall charge of the empirical formula is zero. In a particular embodiment, a is between 0.8 and 1.2, b is between 0.05 and 0.3, c is 0, and d is chosen such that the overall charge of the empirical formula is zero. In a further preferred embodiment, a has the value of 0, b is between 0.04 and 0.1, c is between 0.8 and 1.5, and d is chosen such that the overall charge of the empirical formula is zero.

The oxidation states of the elements are +2 for Cu, +3 for Al, and +2 for Zn. According to the proportion of Mn, the oxidation state for Mn is +2, +3 or +4, where materials may also be present in which one part of the Mn atoms is assigned the +2 oxidation state and others are assigned the +3 or +4 oxidation state, resulting in an average oxidation state in the range from +2 to +4.

Calcium aluminate is a compound containing Ca and Al in the form of oxides and/or hydroxides. For example, it comprises calcined calcium aluminates of the formula x CaO·y Al2O3 or chemically precipitated calcium aluminates of the formula $Ca_xAl_y(OH)_z$. Depending on the treatment of the calcium aluminates, there may alternatively be intermediates between these two empirical formulae that are likewise suitable as binder material. As well as these elements, further elements may be present in the calcium aluminate. In a preferred embodiment, the calcium aluminate contains further elements in a proportion by weight of less than 5.0% by weight, preferably less than 1.0% by weight and more preferably less than 0.1% by weight, based on the weight of the calcium aluminate.

It is a characteristic feature of the shaped catalyst body of the invention that it contains calcium aluminate as binder material in a proportion by weight of 0.5% to 20.0%, based on the shaped catalyst body. The proportion is preferably from 0.5% to 10.0%, more preferably 0.5% to 5.0%, especially preferably from 0.5% to less than 5.0%, most preferably 0.5% to 3.0%, based on the shaped catalyst body.

The atomic Ca/Al ratio of the calcium aluminate which is used in the present invention may vary and is preferably between 0.9 and 3.5, even more preferably between 1.0 and 2.0. Suitable calcium aluminates are synthetically produced materials. Alternatively, it is possible to use naturally occurring calcium aluminates, for example katoite.

The tableted shaped catalyst body may be in various dimensions. The diameter of the tablets may be between 2 and 6 mm and preferably between 2 and 4 mm. The diameter is more preferably 3 mm. The height of the tablets may be between 2 and 6 mm and preferably between 2 and 4 mm. The height is more preferably 3 mm.

Before being used as binder material, the calcium aluminate can be subjected to a thermal treatment (calcination). This takes place at a temperature between 300 and 800° C., preferably between 450 and 750° C. and more preferably between 450 and 650° C. In one embodiment of the invention, the particles of the calcium aluminate have an average particle size with a d50 in the range from 0.1 to 200 µm, preferably in the range from 5 to 50 µm, measured by means of laser sizing to ISO 13302/2009. In a further embodiment, the $d_{90}$ value is in the range from 10 to 300 µm, preferably in the range from 20 to 100 µm.

The shaped catalyst body of the invention comprising a material of the formula $CuAl_aMn_bZn_cO_d$ and comprising calcium aluminate as binder material in a proportion by weight of 0.5% to 20.0%, based on the shaped catalyst body, is prepared by the following steps of the invention:
   a) mixing a metal-containing mixture comprising copper, manganese and at least one element selected from zinc and aluminum with calcium aluminate, a lubricant and water,
   b) tableting the mixture according to step a) to obtain a tableted shaped body,
   c) subjecting the tableted shaped bodies to thermal treatment at a temperature between 200 and 800° C. for a period between 30 min and 4 h, where a is from 0 to 2.5, b is from 0.001 to 0.6 and c is from 0 to 2.5, and d is chosen such that the overall charge of the empirical formula is zero.

In a particular embodiment, a is between 0.8 and 1.2, b is between 0.05 and 0.3, c is 0, and d is chosen such that the overall charge of the empirical formula is zero. In a further preferred embodiment, a has the value of 0, b is between 0.04 and 0.1, c is between 0.8 and 1.5, and d is chosen such that the overall charge of the empirical formula is zero.

In a preferred embodiment, the proportion by weight of the calcium aluminate is from 0.5% to 10.0%, preferably from 0.5% to 5.0%, more preferably from 0.5% to less than 5.0%, most preferably 0.5% to 3.0%, based on the shaped catalyst body.

The mixture comprising copper, manganese and at least one element selected from zinc and aluminum which is used in step a) may be chosen from the group of the oxides, hydroxides and carbonates. The oxides of the corresponding elements are preferentially suitable here. The elements may take the form either of individual compounds, such as copper oxide and oxide of manganese, zinc or aluminum, or of mixed compounds such as mixed oxides of copper, of manganese and at least one element selected from zinc and aluminum.

The metal-containing mixture from step a) can be obtained by the precipitation of the dissolved metal ions from aqueous solution. Suitable starting compounds are in principle all compounds that are soluble in water or basic or acidic aqueous solutions. Preference is given to using nitrates, halides, oxides, sulfates, acetates or formates.

The mixture obtained after step a) can subsequently optionally be subjected to an aging step. The mixture is left to stand here for 5 min to 10 h, preferably for 5 min to 3 h, without adding further components or keeping the mixture in motion. The aging temperature typically corresponds to the ambient temperature of the mixture, but it can be set in a controlled manner within a range from 0° C. to 90° C.

The mixture obtained after step a), which has optionally also been aged, is then, typically without a thermal treatment, optionally compacted and pelletized and then subjected to a tableting step b). This is done using commercial tableting machines, for example of the Pressima type from IMA Kilian. The mixture after step a) contains a lubricant. This is a compound that assists the tableting properties of the mixture. Suitable lubricants are graphite, oils or stearates, preferably graphite. The lubricant is added to the mixture to be tableted in a proportion of 0.1% to 5.0% by weight, preferably from 0.5% to 5.0% by weight and more preferably from 1.0% to 4.0% by weight.

The mixture after step a) also comprises water. This is typically present in an amount of 1% to 10% by weight, based on the metal-containing mixture used, preferably from 2% to 4% by weight, very particularly of 3% by weight.

The thermal treatment of the tablets is effected at a temperature between 200 and 800° C., preferably between 300 and 700° C., more preferably between 300 and 500° C. The duration of this thermal treatment is between 30 min and 4 h, preferably between 1 and 3 h and more preferably 2 h.

The tablets produced by the process of the invention have a side crushing strength of 80 to 300 N, preferably 100 to 250 N, more preferably 120 to 180 N. Preferably, the tablets produced by the tableting have a diameter in the range from 2 to 4 mm, a height in the range from 2 to 4 mm and a side crushing strength in the range from 120 to 180 N.

The pore volume (measured by means of mercury porosimetry) of the shaped catalyst body of the invention is between 100 and 300 $mm^3/g$, preferably between 150 and 250 $mm^3/g$.

The shaped catalyst bodies of the invention have a specific BET surface area of 20 to 60 $m^2/g$, preferably of 30 to 50 $m^2/g$.

Preferably, the proportion of the pore volume of the pores having a radius of 7.0 to 40.0 nm of the shaped catalyst body of the invention is between 50% and 95%, preferably between 70% and 90%, of the total pore volume.

The shaped catalyst body obtainable by the process of the invention is reduced in a further step.

The reduction is preferably effected by heating the tableted shaped catalyst body in a reducing atmosphere. The reducing atmosphere is especially hydrogen. The reduction is effected, for example, at a temperature in the range from 150° C. to 450° C., preferably in the range from 180° C. to 250° C., more preferably in the range from 190° C. to 210° C. The reduction is effected, for example, over a period of 1 hour to 10 days, preferably over a period of 2 hours to 72 hours, more preferably over a period of 24 to 48 hours. In a preferred embodiment, the reducing is effected at a temperature in the range from 190° C. to 210° C. over a period of 24 to 48 hours.

In a preferred embodiment, the shaped catalyst bodies after the reduction are stabilized in wet or dry form. In the case of wet stabilization, the shaped catalyst bodies are blanketed with a liquid in order to minimize contact with oxygen. Suitable liquids include organic liquids and water, preferably organic liquids. Preferred organic liquids are those that have a vapor pressure of 0.5 hPa or less at 20° C. Examples of such suitable organic liquids are isodecanol, Nafol, fatty alcohols, hexadecane, 2-ethylhexanol, propylene glycol and mixtures thereof, particularly isodecanol. In the case of dry stabilization, a mixture of oxygen or an oxygenous gas, preferably air, and an inert gas, such as argon or nitrogen, is meted into the reduction space. The concentration of oxygen in the mixture is preferably increased from about 0.04% by volume to about 21% by volume. For example, a mixture of air and inert gas can be metered in, where the ratio of air to inert gas is initially about 0.2% by volume of air to 99.8% by volume of inert gas. The ratio of air to inert gas is then increased gradually (for example continuously or stepwise) until, ultimately, for example, 100% by volume of air is metered in (corresponding to an oxygen concentration of about 21% by volume). Without being bound to a theory, it is believed that the metered addition of air or oxygen gives rise to a thin oxide layer having a thickness of, for example, 0.5 to 50 nm, preferably 1 to 20 nm, more preferably 1 to 10 nm, at the surface of the catalyst, which protects the shaped catalyst body from further oxidation. In the case of dry stabilization, the reactor temperature is preferably 100° C. or less, more preferably 20° C. to 70° C. and most preferably 30° C. to 50° C. Reduction can be effected ex situ or in situ in the reaction facility which is filled with the shaped catalyst body as catalyst.

The side crushing strength of the shaped catalyst bodies in tablet form, after the reduction, has values of 50 to 250 N, preferably 60 to 200 N, more preferably 70 to 150 N.

To determine the stability of the shaped catalyst bodies of the invention to the action of acid, the shaped body is subjected to an acid treatment and then the side crushing strength of the tablets thus treated is determined.

The shaped catalyst body of the invention is suitable for use in catalytic hydrogenations of carbonyl groups in organic compounds. Possible reactions include the hydrogenation of diesters (especially of maleic esters) to diols, hydrogenation of sugars to polyols, hydrogenation of esters, especially of fatty acid esters, hydrogenation of a fatty acid (for example by esterification and subsequent hydrogenolysis), hydrogenation of a ketone, hydrogenation of oxo aldehydes to oxo alcohols, and the hydrogenation of furfural.

EXAMPLES

The determinations of ignition loss in the context of the present invention were effected by determining the weight of about 1-2 g of a sample of the material to be analyzed and then heating it to 900° C. under ambient atmosphere and storing it at this temperature for 3 h. Subsequently, the sample was cooled down under protective atmosphere and the remaining weight was measured. The difference in weight before and after thermal treatment corresponds to the ignition loss.

Side crushing strength was determined to DIN EN 1094-5. This was done by measuring a statistically sufficient number of tablets (at least 20 tablets) and calculating the arithmetic mean of the individual measurements. This average corresponds to the side crushing strength of a particular sample.

Chemical elements were determined by means of ICP (inductively coupled plasma) measurement to DIN EN ISO 11885.

Acid treatment was effected by blending a total amount of tableted samples of 1.5 g with 15 g of acetic acid (10% by volume in $H_2O$). These were stirred at room temperature for 30 min.

The tableted sample was dried in air at 120° C. for 10 h and then the side crushing strength thereof was measured.

Specific BET surface areas were determined by means of nitrogen adsorption to DIN 66131. The catalyst obtainable by the process of the invention preferably has a BET surface area in the range from 20 to 100 $m^2/g$, especially from 30 to 80 $m^2/g$ and more preferably from 40 to 60 $m^2/g$.

The pore volume of the shaped catalyst body was measured by the mercury porosimetry method to DIN 66133.

The proportion by weight of calcium aluminate in the shaped catalyst body was ascertained by means of x-ray diffractometry. A D4 Endeavor from BRUKER was used. For this purpose, the sample was analyzed over a range from 5 to 90 2° ⊖ (in steps of 0.020 2°⊖, measurement time per step 1.5 seconds). The radiation used was CuKα1 radiation (wavelength 1.54060 Å, 40 kV, 35 mA). During the measurement, the sample stage was rotated about its axis at a speed of 30 revolutions/min. The spectrum of the reflection intensities obtained was quantitatively analyzed by means of Rietveld refinement and the proportion of calcium aluminate in the sample was determined. The proportion of the respective crystal phases was determined using the TOPAS software from BRUKER.

Preparation of the Catalyst Powder

An aqueous solution 1 was prepared by dissolving 1250 g of $Cu(NO_3)_2 \cdot 3\ H_2O$, 220 g of $Mn(NO_3)_2 \cdot 4\ H_2O$ and 1800 g of $Al(NO_3)_3 \cdot 9\ H_2O$ in 9000 g of distilled $H_2O$. Solution 2 was prepared by dissolving 1720 g of $Na_2CO_3$ in 7500 g of distilled $H_2O$. The two solutions were heated separately to 80° C. while stirring. Subsequently, the two solutions were metered into a precipitation vessel with continuous stirring. Both solutions were added here such that a combined mixture in the precipitation vessel had a pH of 7 (+/−0.2). The solid that precipitated out here was filtered off and washed with distilled $H_2O$ in order to remove adhering impurities. The filtercake was resuspended in 8 L of dist. $H_2O$ and spray-dried. The dried powder was then subjected to thermal treatment at 750° C. for 3 h and served as starting material for the tableting examples. The relative proportions by weight were Cu=45% by weight, Mn=7% by weight and Al=18% by weight, based on the total mass after ignition loss. This corresponds to an empirical formula of $CuM_{0.18}Al_{0.94}O_{2.6}$.

Comparative Example 1 (Catalyst A)

Catalyst A was prepared by mixing 500 g of the catalyst powder with 10 g of graphite and then shaping the mixture to tablets having dimensions of height 3 mm and diameter 3 mm. The side crushing strength of the sample was determined after tableting. The acid treatment damaged all tablets such that they were completely in broken form, and determination of the side crushing strength was not possible.

Comparative Example 2 (Catalyst B)

Catalyst B was prepared by mixing 500 g of the catalyst powder with 10 g of graphite and then shaping the mixture to tablets having dimensions of height 4.5 mm and diameter 4.5 mm. The side crushing strength of the sample was determined after tableting and acid treatment. The acid treatment damaged all tablets such that they were completely in broken form, and determination of the side crushing strength was not possible.

A portion of the material obtained after the tableting was subjected to reduction. This involves subjecting the sample to thermal treatment in a gas mixture of 2% by volume of $H_2$ and 98% by volume of $N_2$ at a temperature of 200° C. in order to bring about reduction of the CuO present to Cu. Subsequently, the sample was cooled down to room temperature under nitrogen and stored under liquid decanol. Subsequently, the side crushing strength of this sample was measured.

Example 1 (Catalyst 1)

500 g of the catalyst powder were mixed with 5 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 320° C. The side crushing strength of the sample was determined after tableting, after thermal treatment and after acid treatment.

Example 2 (Catalyst 2)

500 g of the catalyst powder were mixed with 15 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. Thereafter, the tablets were treated with steam at 100-150° C. for 24 h. This was followed by thermal treatment at 320° C. The side crushing strength of the sample was determined after tableting, after thermal treatment and after acid treatment of the calcined sample.

Example 3 (Catalyst 3)

500 g of the catalyst powder were mixed with 15 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 4.5 mm and diameter 4.5 mm. This was followed by thermal treatment at 450° C. The side crushing strength of the sample was determined after tableting, after thermal treatment and after acid treatment of the calcined sample.

A portion of the material obtained after the tableting was subjected to reduction. This involves subjecting the sample to thermal treatment in a gas mixture of 2% by volume of $H_2$ and 98% by volume of $N_2$ at a temperature of 200° C. in order to bring about reduction of the CuO present to Cu. Subsequently, the sample was cooled down to room temperature under nitrogen and stored under liquid decanol. Subsequently, the side crushing strength of this sample was measured.

Example 4 (Catalyst 4)

500 g of the catalyst powder were mixed with 15 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 450° C. The side crushing strength of the sample was determined after tableting, after thermal treatment and after acid treatment of the calcined sample.

Example 5 (Catalyst 5)

500 g of the catalyst powder were mixed with 15 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 650° C. The side crushing strength of the sample was determined after tableting, after thermal treatment and after acid treatment of the calcined sample.

Example 6 (Catalyst 6)

500 g of the catalyst powder were mixed with 50 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 450° C. The side crushing strength of the sample was determined after tableting, after thermal treatment and after acid treatment of the calcined sample.

Example 7 (Catalyst 7)

500 g of the catalyst powder were mixed with 50 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 650° C. The side crushing strength of the sample was determined after tableting, after thermal treatment and after acid treatment of the calcined sample.

Example 8 (Catalyst 8)

500 g of the catalyst powder were mixed with 100 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 450° C. The side crushing strength of the sample was determined after tableting, after thermal treatment and after acid treatment of the calcined sample.

Example 9 (Catalyst 9)

500 g of the catalyst powder were mixed with 100 g of calcium aluminate (SECAR 71, 30% by weight of CaO, 70% by weight of $Al_2O_3$), 10 g of graphite and 15 g of distilled $H_2O$. Subsequently, the mixture was aged for 4 h and shaped to tablets having dimensions of height 3 mm and diameter 3 mm. This was followed by thermal treatment at 650° C. The side crushing strength of the sample was determined after tableting, after thermal treatment and after acid treatment of the calcined sample.

Example 10 (Catalyst 10)

The calcium aluminate used in example 1 was subjected to thermal treatment at 650° C. for 2 h. Subsequently, 500 g of the catalyst powder were mixed with 15 g of this thermally treated calcium aluminate, 10 g of graphite and 15 g of distilled $H_2O$. Subsequently, the mixture was aged for 4 h and shaped to tablets having dimensions of height 3 mm and diameter 3 mm. This was followed by thermal treatment at 450° C. The side crushing strength of the sample was determined after tableting, after thermal treatment and after acid treatment of the calcined sample.

Example 11 (Catalyst 11)

The calcium aluminate used in example 1 was subjected to thermal treatment at 650° C. for 2 h. Subsequently, 500 g of the catalyst powder were mixed with 15 g of this thermally treated calcium aluminate, 10 g of graphite and 15 g of distilled $H_2O$. Subsequently, the mixture was aged for 4 h and shaped to tablets having dimensions of height 3 mm and diameter 3 mm. This was followed by thermal treatment at 650° C. The side crushing strength of the sample was determined after tableting, after thermal treatment and after acid treatment of the calcined sample.

| Example | Calcium aluminate [% by wt.] | Thermal treatment temperature [° C.] | Side crushing strength after tableting [N] | Side crushing strength after thermal treatment [N] | Side crushing strength after acid treatment [N] | Side crushing strength after reduction [N] | Dimensions [mm × mm] | Rel. pore volume of the pores in the range of radii of 40-7.0 nm [%] | BET surface area [m²/g] |
|---|---|---|---|---|---|---|---|---|---|
| Catalyst A | — | no thermal treatment | 85 | — | 0 | 0 | 3 × 3 | 69.6 | 57 |
| Catalyst B | — | no thermal treatment | 99 | — | 0 | 69 | 4.5 × 4.5 | 87.3 | 57 |
| Catalyst 1 | 1 | 320 | 64 | 151 | 129 | not determined | 3 × 3 | 71.7 | 53 |
| Catalyst 2 | 3 | 320 | 73 | 162 | 109 | not determined | 3 × 3 | 74.8 | 53 |
| Catalyst 3 | 3 | 450 | 82 | 230 | 190 | 134 | 4.5 × 4.5 | 83.1 | 39 |
| Catalyst 4 | 3 | 450 | 88 | 175 | 122 | not determined | 3 × 3 | 87.3 | 41 |
| Catalyst 5 | 3 | 650 | 88 | 233 | 170 | not determined | 3 × 3 | 87.5 | 35 |
| Catalyst 6 | 10 | 450 | 66 | 134 | 93 | not determined | 3 × 3 | 84.7 | 44 |
| Catalyst 7 | 10 | 650 | 70 | 175 | 141 | not determined | 3 × 3 | 87.1 | 36 |
| Catalyst 8 | 20 | 450 | 70 | 122 | 90 | not determined | 3 × 3 | 82.0 | 39 |
| Catalyst 9 | 20 | 650 | 71 | 161 | 140 | not determined | 3 × 3 | 78.0 | 35 |
| Catalyst 10 | 3 | 450 | 90 | 216 | 145 | not determined | 3 × 3 | 89.5 | 40 |
| Catalyst 11 | 3 | 450 | 104 | 253 | 165 | not determined | 3 × 3 | 86.3 | 40 |

It is clearly apparent from table 1 that the catalysts of the invention after the thermal treatment have a much higher side crushing strength than the comparative catalyst. After the acid treatment, there is a decrease in the side crushing strength for all samples, the side crushing strength of the samples of the invention still being much higher than that of the comparative catalysts catalyst A and B prior to the acid treatment. This underlines the elevated mechanical stability of the catalysts of the invention even under the severe conditions of an acid-containing environment as in the case of a hydrogenation of carbonyl groups in organic compounds such as esters, diesters, aldehydes or ketones since the reactants contain acidic impurities.

The specific BET surface areas are not significantly affected by the process of the invention. The same is also true of the relative pore volume of the pores in the range of 40-7.0 nm. This underlines the stability of the shaped catalyst bodies of the invention to thermal stress during the thermal treatment.

The invention claimed is:

1. A shaped catalyst body comprising
a material of the formula $CuAl_aMn_bO_d$ where a is a number greater than 0 and up to 2.5 and b is a number between 0.001 and 0.6, and d is chosen such that the overall charge of the empirical formula is zero; and
a calcium aluminate binder, present in the shaped catalyst body as a phase distinct from the material of the formula $CuAl_aMn_bO_d$, in an amount by weight of 0.5 to 20.0%;
wherein the shaped catalyst body is in tablet form.

2. The shaped catalyst body as claimed in claim 1, wherein the calcium aluminate binder is present in the shaped catalyst body in an amount by weight of 0.5% to 10.0%.

3. The shaped catalyst body as claimed in claim 1, wherein the side crushing strength is 100-300 N, determined according to DIN EN 1094-5.

4. A process for producing a shaped catalyst body comprising the following steps:
mixing a metal-containing mixture comprising copper, manganese and aluminum with calcium aluminate, a lubricant and water;
tableting the mixture of the metal-containing mixture, a calcium aluminate binder, lubricant, and water to obtain a tableted shaped body; and
subjecting the tableted shaped body to thermal treatment at a temperature between 200 and 800° C. for a period between 30 min and 4 h,
wherein the tableted shaped body after thermal treatment comprises
a material of the formula $CuAl_aMn_bO_d$, where a is between greater than 0 and up to 2.5 and b is between 0.001 and 0.6, and d is chosen such that the overall charge of the empirical formula is zero; and
the calcium aluminate binder, present in the shaped body as a phase distinct from the material of the formula $CuAl_aMn_bO_d$, in an amount by weight of 0.5 to 20.0%.

5. The process as claimed in claim 4, wherein the metal-containing mixture is a mixed oxide of copper, manganese and aluminum.

6. The process as claimed in claim 5, wherein the calcium aluminate binder is present in the shaped catalyst body in an amount by weight of 0.5% to 10.0%.

7. The process as claimed in claim 4, further comprising
after mixing the metal-containing mixture with the calcium aluminate binder, lubricant and water, aging the mixture for a period of 5 min to 10 h at a temperature in the range of 0° C. to 90° C.; and then
tableting the aged mixture.

8. The process as claimed in claim 4, wherein the thermal treatment takes place between 300 and 500° C. for a period between 1 h and 3 h.

9. The process as claimed in claim 4, wherein the calcium aluminate mixed with the metal-containing mixture, lubricant and water is essentially in oxidic form.

10. The process as claimed in claim 4, further comprising after subjecting the tableted shaped body to thermal treatment, reducing the shaped body.

11. A process for hydrogenating carbonyl groups in organic compounds with the shaped catalyst body as claimed in claim 1.

12. The shaped catalyst body as claimed in claim 1, wherein elements other than Ca, Al, O, and H are present in the calcium aluminate binder in an amount by weight of less than 5.0%.

13. The shaped catalyst body as claimed in claim 1, wherein elements other than Ca, Al, O, and H are present in the calcium aluminate binder in an amount by weight of less than 1.0%.

14. The shaped catalyst body as claimed in claim 1, wherein the atomic Ca/Al ratio of the calcium aluminate binder is between 0.9 and 3.5.

15. The shaped catalyst body as claimed in claim 1, wherein the calcium aluminate binder comprises calcium aluminate particles having an average particle size ($D_{50}$) in the range of 0.1 to 200 µm.

16. The shaped catalyst body as claimed in claim 1, wherein the calcium aluminate binder is present in the shaped catalyst body in an amount by weight of 0.5% to 5.0%.

17. The shaped catalyst body as claimed in claim 1, wherein a is between 0.8 and 1.2, and b is between 0.05 and 0.3.

18. The process as claimed in claim 5, wherein the calcium aluminate binder is present in the shaped catalyst body in an amount by weight of 0.5% to 5.0%.

* * * * *